(12) United States Patent
Adkins, Jr. et al.

(10) Patent No.: US 8,663,717 B2
(45) Date of Patent: Mar. 4, 2014

(54) METHODS AND DELIVERY VEHICLES FOR PROVIDING THROAT RELIEF

(75) Inventors: Nat Adkins, Jr., Richmond, TX (US);
Cynthia Barratt, Richmond, TX (US);
Fabiana Banov, Sugar Land, TX (US);
Kaitlin Hopkins, San Marcos, TX (US);
James Walter Price, San Marcos, TX (US)

(73) Assignee: Fontus Science, LLC, Fulshear, TX (US)

( * ) Notice: Subject to any disclaimer, the term of this patent is extended or adjusted under 35 U.S.C. 154(b) by 0 days.

(21) Appl. No.: 13/357,013

(22) Filed: Jan. 24, 2012

(65) Prior Publication Data
US 2013/0189357 A1    Jul. 25, 2013

(51) Int. Cl.
*A61K 36/254*    (2006.01)
*A61K 36/258*    (2006.01)

(52) U.S. Cl.
USPC ........................................................ 424/728

(58) Field of Classification Search
None
See application file for complete search history.

(56) References Cited

U.S. PATENT DOCUMENTS

| | | | |
|---|---|---|---|
| 3,511,914 A | 5/1970 | Wolkoff | |
| 6,197,334 B1 | 3/2001 | Renda | |
| 7,226,590 B2 | 6/2007 | Chilcott et al. | |
| 7,879,354 B2 * | 2/2011 | Rinker et al. | 424/473 |
| 2006/0068005 A1 * | 3/2006 | Ross et al. | 424/464 |
| 2007/0231389 A1 * | 10/2007 | Bunick et al. | 424/472 |
| 2008/0254079 A1 * | 10/2008 | Ferrari | 424/401 |
| 2008/0292715 A1 * | 11/2008 | Snow et al. | 424/539 |
| 2011/0117071 A1 | 5/2011 | Barrett et al. | |
| 2011/0263528 A1 | 10/2011 | Keiji et al. | |

FOREIGN PATENT DOCUMENTS

| | | | |
|---|---|---|---|
| CN | 1685985 A | * | 10/2005 |
| CN | 101253981 A | * | 9/2008 |
| EP | 669130 A1 | * | 8/1995 |
| RU | 2083123 C1 | * | 7/1997 |
| SG | 170414 A | | 5/2011 |
| WO | 2010044042 A1 | | 4/2010 |

OTHER PUBLICATIONS

Glycerine: an overview, The Soap and Detergent Association Glycerine & Oleochemical Division, New York: pp. 1-27, 1990.
H.J. Peppler, A Bacteriological Comparison Between Synthetic and Natural Glycerol, Journal of Bacteriology 44(2): pp. 233-236, Oct. 24, 1941.
Glycerol, Wikipedia, last updated Jun. 11, 2013; http://en.wikipedia.org/wiki/Glycerol.

* cited by examiner

*Primary Examiner* — Amy L Clark
(74) *Attorney, Agent, or Firm* — D'Ambrosio & Menon, PLLC; Usha Menon

(57) ABSTRACT

A troche for providing throat relief. The troche includes a solid base containing pectin, food flavoring, aloe vera powder 200:1, malic acid, ginseng extract, natural glycerin, manuka honey, orchid extract, lysozyme, sorbitol crystals, and sorbitol base.

12 Claims, 3 Drawing Sheets

METHODS AND DELIVERY VEHICLES FOR PROVIDING THROAT RELIEF

FIELD OF THE INVENTION

The invention relates generally to methods and delivery vehicles for providing throat relief. More particularly, the invention relates to troches and methods of using the same for providing throat relief.

BACKGROUND

A troche, or a throat lozenge, is a small, medicated tablet designed to dissolve slowly in one's mouth. Troches are commonly used to soothe a sore throat and/or inhibit a cough. However, depending on the troche's composition, it may be used to treat other medical conditions. Typical ingredients include menthol, pectin, benzocaine, eucalyptus oil, and honey.

Honey is an effective ingredient for certain applications of troches because of its natural antibacterial properties. Manuka honey, in particular, exhibits desirable antibacterial properties.

Manuka honey is produced by bees that frequent the manuka bush, *Leptospermum scoparium*, indigenous to New Zealand. Because of its uniquely high concentration of non-peroxide activity (NPA) components, manuka honey provides several advantages over the hydrogen peroxide-based antibacterial properties offered by other types of honey. For example, unlike the hydrogen peroxide-based antibacterial activity of other types of honey, the non-peroxide type of antibacterial activity found in manuka honey is not degraded by the catalase enzyme present in body tissue and serum, and it is not destroyed when exposed to heat and/or light or when it is deprived of oxygen.

SUMMARY

One or more embodiments of the invention relate to a troche for providing throat relief. The troche may have a solid base having a substantially smooth outer surface. The solid base may be disc-shaped. The diameter of the solid base may range from about 1.5 mm to about 2 mm. The thickness of the solid base may range from about 0.3 mm to about 0.6 mm.

In one or more embodiments, the solid base may define one or more dimples. Each dimple may be disposed at a diametrical side of the solid base. The diameter of each dimple may range from about 1 mm to about 1.2 mm. The maximum depth of each dimple may range from about 0.1 mm to about 0.4 mm.

In one or more embodiments, one or more edges of the troche are filleted. For example, all edges of the troche may be filleted. The troche may comprise a color selected from a group consisting of: green, red, orange and yellow. Further, the troche may comprise a flavor selected from a group consisting of: apple, peppermint, spearmint orange, tangerine, honey, ginger and licorice.

In one or more embodiments, the solid base may comprise, consist essentially of, and/or consist of one or more components selected from the following group: about 0.009 wt. % to about 0.011 wt. % pectin; about 0.90 wt. % to about 1.10 wt. % food flavoring; about 0.18 wt. % to about 0.22 wt. % *aloe vera* powder 200:1; about 0.90 wt. % to about 1.10 wt. % malic acid; about 0.18 wt. % to about 0.22 wt. % ginseng extract; about 2.70 wt. % to about 3.30 wt. % natural glycerin; about 4.50 wt. % to about 5.50 wt. % manuka honey; about 0.045 wt. % to about 0.055 wt. % orchid extract; about 0.009 wt. % to about 0.011 wt. % lysozome; about 1.80 wt. % to about 2.20 wt. % sorbitol crystals; and quantum sufficit wt. % sorbitol base.

In one or more embodiments, the solid base may comprise, consist essentially of, and/or consist of one or more components selected from the following group: about 0.01 wt. % pectin; about 1.00 wt. % food flavoring; about 0.20 wt. % *aloe vera* powder 200:1; about 1.00 wt. % malic acid; about 0.20 wt. % ginseng extract; about 3.00 wt. % natural glycerin; about 5.00 wt. % manuka honey; about 0.01% orchid extract; about 0.01 wt. % lysozome; about 2.00 wt. % sorbitol crystals; and quantum sufficit wt. % sorbitol base.

In one or more embodiments, the solid base may comprise: about 0.01 wt. % pectin; about 1.00 wt. % food flavoring; about 0.20 wt. % *aloe vera* powder 200:1; about 1.00 wt. % malic acid; about 0.20 wt. % ginseng extract; about 3.00 wt. % natural glycerin; about 5.00 wt. % manuka honey; about 0.01% orchid extract; about 0.01 wt. % lysozome; about 2.00 wt. % sorbitol crystals; and quantum sufficit wt. % sorbitol base.

One or more embodiments of the invention relate to a method of soothing a subject's throat. The method involves disposing the troche, according to one or more embodiments described herein, in the subject's mouth. The method further involves dissolving the troche.

In one or more embodiments, the dissolving the troche may occur while the troche is in the subject's mouth. The duration of the dissolution of the troche may range from about 10 minutes to about 30 minutes.

DETAILED DESCRIPTION OF THE INVENTION

One or more embodiments of the present invention relate to delivery vehicles for providing throat relief. Throughout this application, a troche, or a throat lozenge, is described as a delivery vehicle for providing throat relief. However, any other delivery vehicle consistent with the geometry and/or the composition of embodiments of the troche may be used for the same purpose and should be considered embodiments of the invention.

Figure 1:
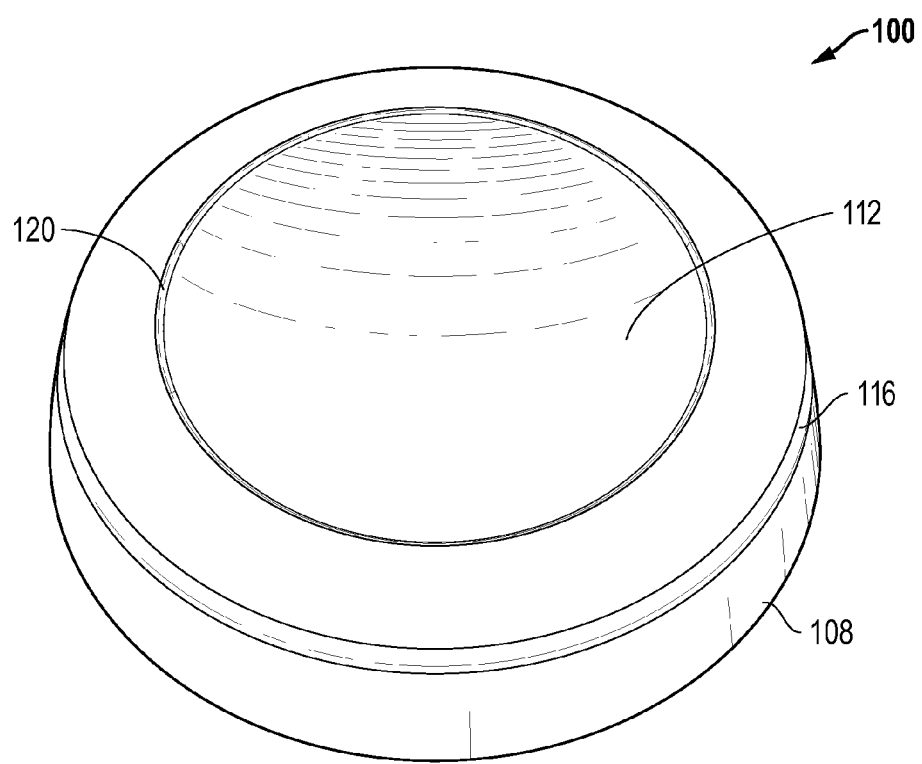
FIG. 1 shows a perspective view of a troche in accordance with one or more embodiments of the present invention.
Figure 2:
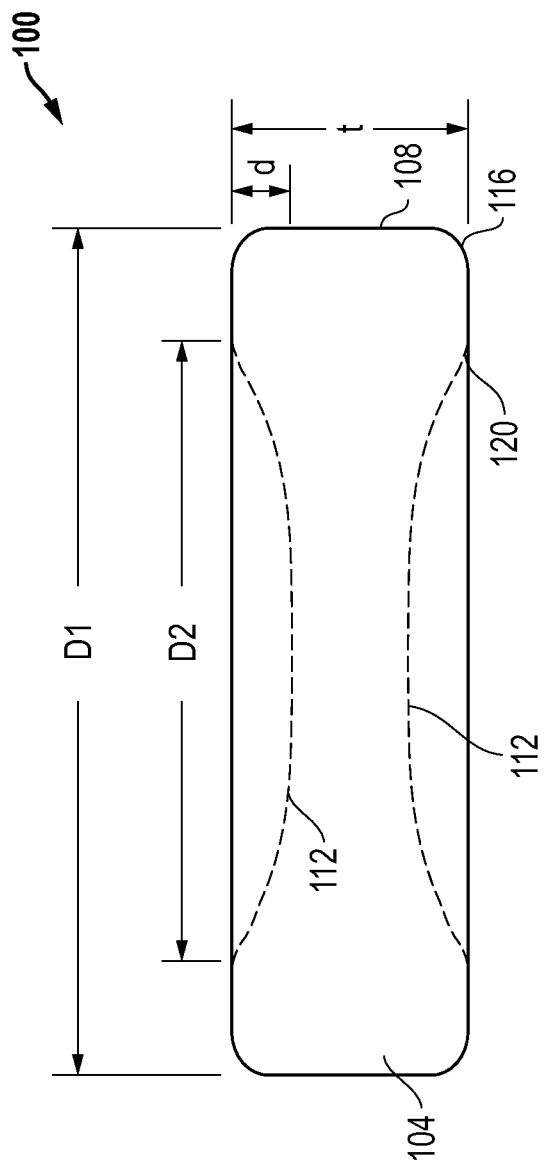
FIG. 2 shows a side view of a troche in accordance with one or more embodiments of the present invention.

FIGS. 1-2 illustrate a perspective view and a side view, respectively, of a troche 100 in accordance with one or more embodiments of the invention. The troche 100 may be disc-shaped, with a solid base 104 and smooth outer surface 108. The outer surface 108 of the troche 100 may maintain a smooth texture as it dissolves in the mouth.

The troche 100 may have a diameter 'D1' ranging from about 1.5 mm to about 2 mm and a thickness 't' ranging from about 0.3 mm to about 0.6 mm.

A dimple 112 may be centrally disposed at each side of the disc-shaped troche 100. The dimples 112 may each have a diameter 'D2' of from about 1 mm to about 1.2 mm. Each dimple 112 may have a maximum depth 'd' ranging from about 0.1 mm to about 0.4 mm.

The outer edges 116 of the disc-shaped troche 100 may be filleted. The radius of the filleted outer edges 116 may range from about 2 mm to about 4 mm. Similarly, the inner edges 120 of the disc-shaped troche 100, disposed at the perimeter of the dimples 112, may be filleted. The radius of the filleted inner edges 120 may range from about 1 mm to about 4 mm.

Thus, the troche 100 may have rounded edges throughout its outer geometry. In conjunction with the smooth texture of its outer surface 108, the troche's rounded edges may offer a comfortable hold in the mouth. The concavity provided by the dimples 112 may complement the natural pliable convexity of the tongue (and other anatomy within the mouth), thereby facilitating improved control of the troche's 100 placement within the mouth. As a result, a person may be able to speak and/or sing clearly (i.e., substantially similar to the clarity the person would achieve without the troche 100), even while consuming the troche 100.

Designed to dissolve slowly, the troche 100 may provide throat relief for up to 1 to 3 hours.

Embodiments of the present invention also relate to compositions for providing throat relief. In one or more embodiments, a composition may comprise, consist essentially of, and/or consist of one or more components selected from the following group: pectin, food flavoring, aloe vera powder 200:1, malic acid, ginseng extract, natural glycerin, manuka honey, orchid extract, lysozyme, sorbitol crystals, and sorbitol base. In one or more embodiments, malic acid can be substituted with citric acid.

Manuka honey contains some antibacterial activity. Malic acid may stimulate the salivary glands thereby increasing saliva production. Aloe Vera and glycerin may promote moisture to the throat. Ginseng is a stimulating substance that also helps to decrease cough symptoms. The unique combination of these ingredients more effectively relieves dry throat symptoms and also increases salivation. In one or more embodiments, the composition may comprise, consist essentially of, and/or consist of one or more components selected from the following group: about 0.009 wt. % to about 0.011 wt. % pectin, about 0.90 wt. % to about 1.10 wt. % food flavoring, about 0.18 wt. % to about 0.22 wt. % aloe vera powder 200:1, about 0.90 wt. % to about 1.10 wt. % malic acid, about 0.18 wt. % to about 0.22 wt. % ginseng extract, about 2.70 wt. % to about 3.30 wt. % natural glycerin, about 4.50 wt. % to about 5.50 wt. % manuka honey, about 0.045 wt. % to about 0.055 wt. % orchid extract, about 0.009 wt. % to about 0.011 wt. % lysozyme, about 1.80 wt. % to about 2.20 wt. % sorbitol crystals, and quantum sufficit wt. % sorbitol base.

In yet other embodiments, the composition may comprise, consist essentially of, and/or consist of one or more components selected from the following group: 0.01 wt. % pectin, 1.00 wt. % food flavoring, 0.20 wt. % aloe vera powder 200:1, 1.00 wt. % malic acid, 0.20 wt. % ginseng extract, 3.00 wt. % natural glycerin, 5.00 wt. % manuka honey, 0.05 wt. % orchid extract, 0.01 wt. % lysozyme, 2.00 wt. % sorbitol crystals, and quantum sufficit wt. % sorbitol base. Food flavoring may be added to impart a desired flavor to the troche. In one embodiment of the invention, an apple flavor may be imparted to the troche. For example, the apple flavor may be imparted by adding an artificial flavor and propyleneglycol.

The sorbitol base is melted until 160° C. and the active ingredients are added at a temperature of 90° C. After that the final formula is added to the mold to congeal.

Embodiments of the present invention further relate to methods of providing throat relief.

Figure 3:
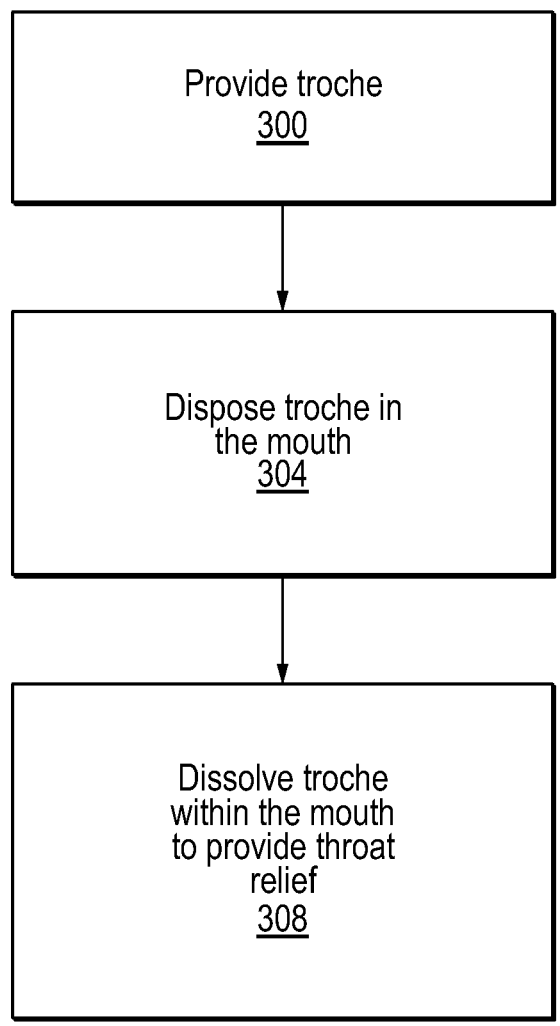
FIG. 3 shows a flow chart illustrating a method in accordance with one or more embodiments of the present invention.

As illustrated in the flow chart of FIG. 3, a method of providing throat relief in accordance with one or more embodiments of the invention involves the following steps. In step 300, a delivery vehicle is provided. In one or more embodiments, the delivery vehicle may be a troche, or a lozenge, having the geometry and composition described above with reference to FIGS. 1-2.

In step 304, the troche is disposed in the mouth. The troche may be maneuvered within the mouth to a comfortable position.

In step 308, the troche is dissolved within the mouth. In one or more embodiments, the troche may be designed to dissolve slowly. Dissolution time is a function of the troche size. When dissolved, the components of the troche may comprise a runny consistency, which may reach the throat.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

The invention claimed is:

1. A troche for providing dry throat relief and stimulating saliva production, comprising: a solid base, the solid base consisting essentially of:
   about 0.009 wt. % to about 0.011 wt. % pectin;
   about 0.90 wt. % to about 1.10 wt. % food flavoring;
   about 0.18 wt. % to about 0.22 wt. % aloe vera powder 200:1;
   about 0.90 wt. % to about 1.10 wt. % malic acid;
   about 0.18 wt. % to about 0.22 wt. % ginseng extract;
   about 2.70 wt. % to about 3.30 wt. % natural glycerin;
   about 4.50 wt. % to about 5.50 wt. % manuka honey;
   about 0.045 wt. % to about 0.055 wt. % orchid extract;
   about 0.009 wt. % to about 0.011 wt. % lysozome;
   about 1.80 wt. % to about 2.20 wt. % sorbitol crystals; and
   quantum sufficit wt. % sorbitol base.

2. The troche of claim 1, wherein the solid base has a substantially smooth outer surface.

3. The troche of claim 1, wherein the solid base has a disc shape.

4. The troche of claim 1, wherein the solid base has a diameter ranging from about 1.5 mm to about 2 mm.

5. The troche of claim 1, wherein the solid base has a thickness ranging from about 0.3 mm to about 0.6 mm.

6. The troche of claim 1, wherein the solid base contains one or more dimples, each dimple centrally disposed at a diametrical side of the solid base.

7. The troche of claim 6, wherein each dimple comprises a diameter of from about 1 mm to about 1.2 mm.

8. The troche of claim 6, wherein each dimple comprises a maximum depth ranging from about 0.1 mm to about 0.4 mm.

9. The troche of claim 1, wherein the solid base has filleted edges.

10. The troche of claim 1, wherein the troche has a color selected from the group consisting of: green, red, orange and yellow.

11. The troche of claim 1, wherein the troche has a flavor selected from the group consisting of: apple, peppermint, spearmint orange, tangerine, honey, ginger and licorice.

12. The troche of claim 10, wherein the troche has a flavor selected from the group consisting of: apple, peppermint, spearmint orange, tangerine, honey, ginger and licorice.

* * * * *